United States Patent [19]

Krbechek

[11] 4,255,345
[45] Mar. 10, 1981

[54] STEROID PRODUCTION

[75] Inventor: Leroy O. Krbechek, Minneapolis, Minn.

[73] Assignee: Henkel Corporation, Minneapolis, Minn.

[21] Appl. No.: 122,397

[22] Filed: Feb. 19, 1980

[51] Int. Cl.³ .............................................. C07J 9/00
[52] U.S. Cl. .............................. 260/397.1; 260/397.3
[58] Field of Search ..................... /Steroids MS File; 260/397.1, 397.3

[56] References Cited

U.S. PATENT DOCUMENTS 4,191,759  3/1980  Johnston et al. ................. 260/239.5

OTHER PUBLICATIONS

Robinson et al., "JACS" (1956) p. 524.

Primary Examiner—Elbert L. Roberts
Attorney, Agent, or Firm—Forrest L. Collins; Patrick J. Span

[57] ABSTRACT

The present invention discusses the production of useful steroids through starting with a steroid which has an acid side chain attached to the steroid ring structure. The present invention also describes and claims several novel compounds obtained through the described process.

37 Claims, No Drawings

STEROID PRODUCTION

BACKGROUND OF THE INVENTION

1. Field of the Invention

The present invention describes methods for obtaining useful steroids such as progesterone.

2. Description of the Art

This invention deals basically with the conversion of steroid compounds having an acid side chain to give useful intermediates and end compounds such as progesterone.

For instance, in published European patent application 4-913 dated Oct. 31, 1979, it was revealed that through microbiological transformation that it was possible to obtain a substantial yield of steroids having a 20 carbonyl functionality. It has also been observed that through following the teachings of the European patent that it is also possible to obtain 3-oxo-pregna-1,4,17(20)-triene-20-carboxylic acid. Of course, depending upon the pH of the solution, it is possible to obtain the carbonyl compounds as either the acid or salt or mixtures thereof.

Jiu, et al, in U.S. Pat. No. 3,994,933, issued Nov. 30, 1976, describes the process of obtaining 3-oxo-pregna-4,17(20)-diene-20-carboxylic acid and its esters through microbiological degradation of several basic sterols. Previously, Julian in *JACS* Vol. 70, published Apr. 3, 1948, No. 3, at page 887, describes several steroids having an acid functionality in the side chain. Steroidal acids and their derivatives are discussed in U.S. Pat. No. 4,088,760 issued to Benson, et al., on May 9, 1978.

Derivatives of steroids are discussed in U.S. Pat. No. 2,566,336 issued to Julian, et al., Sept. 4, 1951, and in British Pat. No. 1,043,018 to Meyer, et al., published Sept. 21, 1966. Ruschig, et al, discusses steroids in U.S. Pat. No. 2,731,461 issued Jan. 17, 1956, and in an article published Feb. 21, 1955, in Chemische Berichte Jahrg.88, Number 6, 1955, pages 883–894. Additional steroid products are discussed in U.S. Pat. No. 2,752,369 issued to Holysz et al, on June 26, 1956 and U.S. Pat. No. 3,519,658 issued July 7, 1970 to Adam, et al.

Still more steroids are reported in "The Oxidation of Steroidal Amines to Nitro Steroids" by Robinson, et al, Volume 31, J. Am. Chem. Soc. 1956, p.524 et seq. A second article discussing amine steroids is found at Tetrahedron Letters, No. 18, pp. 1053–1061 (1964) by Tomita, et al. Amines are generally discussed by Corey, et al, J. Am. Chem. Soc., Vol. 91, #6, pp. 1429–32 (1969), and by Dinizo, et al, at J. Am. Chem. Soc., Vol. 97 #23, pp. 6900–6901 (1975).

Additional references which discuss compounds having acid side chains and their conversion into useful steroids include the article of Wieland, et al, published in Helvetica Chimica Acta, Vol. 32, part V (1949) No. 233 at page 1764. In another article in the same journal, steroids having an acid side chain are described by Meystre, et al, at Helvetica Chimica Acta, Vol. 32, part V (1949) No. 232 at page 1758. Similarly, Wieland, et al, at Helvetica Chimica Acta, Vol. 32, Part VI, (1949, No. 255 at page 1922 again describes the transformation of steroids having an acid side chain.

To the extent that each of the foregoing references are applicable to the present invention, they are herein incorporated by reference.

Throughout the present invention, percentages and ratios are given by weight unless otherwise indicated and temperatures are in degrees Celsius unless otherwise indicated.

SUMMARY OF THE INVENTION

In its most basic aspect the present invention describes a process for the production of an amido-steroidal compound selected from the group consisting of 3-oxo-pregna-1,4-diene-20-carboxylic acid amide; 3-oxo-pregn-4-ene-20-carboxylic acid amide; 3-oxo-pregna-1,4,17(20)-triene-20-carboxylic acid amide; and 3-oxo-pregna-4,17(20)-diene-20-carboxylic acid amide and mixtures thereof comprising:

(a) reacting a member selected from the group consisting of the parent acid of the amido-steroidal compound and mixtures thereof with a sufficient amount of an inorganic halogenating agent to obtain the corresponding carbonyl halide; and, (b) reacting the carbonyl halide formed in (a) in the presence of a source of ammonia in a sufficient amount, to form the 3-oxo-pregna-1,4-diene-20-carboxylic acid amide; 3-oxo-pregn-4-ene-20-carboxylic acid amide; 3-oxo-pregna-1,4,17(20)-triene-20-carboxylic acid amide; and 3-oxo-pregna-4,17(20)-diene-20-carboxylic acid amide and mixtures thereof thereby obtaining the desired amido-steroid.

The present invention further describes a process for the production of a member selected from the group consisting of 20-isocyanato-3-oxo-pregna-1,4-diene; 20-isocyanato-3-oxo-pregn-4-ene; 20-isocyanato-3-oxo-pregna-1,4,17(20)-triene and 20-isocyanato-3-oxo-pregna-4,17(20)-diene and mixtures thereof from a member selected from the group consisting of 3-oxo-pregna-1,4-diene-20-carboxylic acid amide; 3-oxo-pregna-1,4,17(20)-triene-20-carboxylic acid amide; 3-oxo-pregna-4,17(20)-diene-20-carboxylic acid amide and 3-oxo-pregn-4-ene-20-carboxylic acid amide and mixtures thereof comprising:

(a) reacting the amide in the presence of a sufficient quantity of lead tetraacetate in the presence of a non-aqueous aprotic solvent;

(b) thereafter, removing the solvent from the product thereby obtaining the corresponding isocyanate compound.

The present invention further describes the process for the production of a carbonyl halide selected from the group consisting of 3-oxo-pregna-1,4-diene-20-carboxylic acid halide; 3-oxo-pregn-4- ene-20-carboxylic acid halide; 3-oxo-pregna-1,4,17(20)-triene-20-carboxylic acid halide; and 3-oxo-pregna-4,17(20)-diene-20-carboxylic acid halide and mixtures thereof comprising reacting the corresponding carboxylic acid with an inorganic halogenating agent to produce the carbonyl halide.

DETAILED DESCRIPTION OF THE INVENTION

In the first aspect of the present invention, one of several acids having a steroidal functionality at the 20-carbon position or salt or hydrolyzable ester thereof is reacted with an inorganic halo-genating agent to obtain the corresponding carbonyl halide. Inorganic halogenating agents are employed to facilitate greater yields, ease of product separation and to lessen the possibility that an unwanted side reaction will occur.

In practice, the acids with which the present invention are concerned or their salts or hydrolyzable esters, are (A) 3-oxo-pregna-1,4,diene-20-carboxylic acid; (B) 3-oxo-pregn-4-ene-20-carboxylic acid, (C) 3-oxo-pregna-1,4,17(20)-triene-20-carboxylic acid and (D) 3-oxo-pregna-4,17(20)-diene-20-carboxylic acid and mixtures thereof.

In particular inorganic halogenating agents utilized in the present invention include such commercially obtainable materials as thionyl chloride, thionyl bromide, thionyl fluoride, phosphorus trichloride, phosphorus pentachloride, phosphorus pentabromide, phosphorus oxychloride, and phosphorus oxybromide. The preferred materials are the thionyl compounds. It has been observed that the halogenating agent is preferably a chlorinating agent and in order of preference thionyl chloride is superior to the remaining listed chlorinating agents. To a large degree, however, it will be observed that the particular halogenating agent employed may depend upon solvent conditions, convenience of reaction and tolerance of the steroid ring structure to the particular halogenating agent.

Shown below are structural formulas A, B, C, D, corresponding to the structure of the respective starting acids described above.

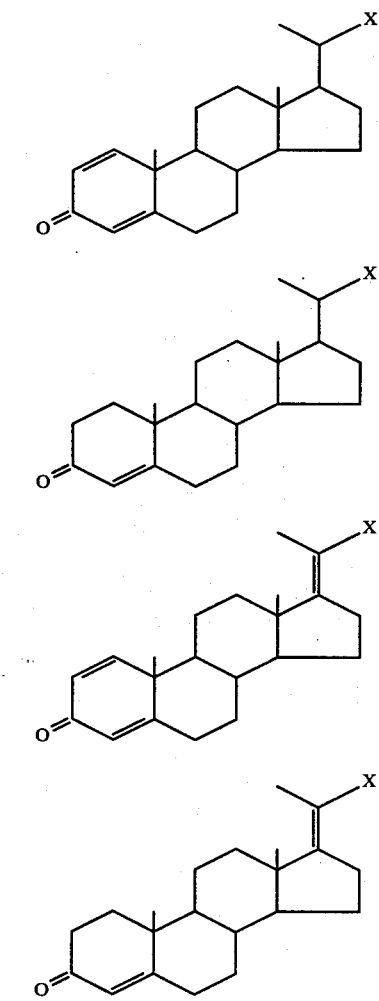

In the above formulas X is COOH where the acid is employed; COOR where an ester or salt is utilized, and CONH₂ where the amide is used; COCl where the acid chloride is described and NCO where the isocyanate is intended. Where X is NH₂, the amine is shown. Where X is N(CO)OR or N(CO)O(CO)R the carbamic acid esters and anhydrides are shown respectively.

The process for conducting the halogenation of the particular starting steroid compound is generally as follows. The starting steroid is mixed at a temperature of from about −20° C., to about 75° C., preferably at from about 0° C. to about 20° C., with at least an equivalent quantity of the halogenating agent required to effect the formation of the carbonyl halide of the steroid.

For the sake of convenience, however, substantial quantities of the halogenating agent over and above that required on a stoichiometric basis may be employed in the present invention. Convenient amounts include from from 1.1 to 5.0 equivalents of the halogenating agent per mole of the starting acid. A more preferable range is from 1.2 equivalents to 3.0 equivalents of the halogenating agent. The use of inorganic halogenating agents allows for rapid acid halide formation without the difficulties associated with the use of organic halogenating agents.

The reaction of the halogenating agent and the steroidal acid are such that the reaction is conveniently conducted at atmospheric pressure. Conveniently, the halogenating agent is added to the larger dominant solution of the steroidal compound. Convenient solvents for use in this reaction include any commonly used solvents which are not reactive with the acid halide, the starting steroid or the halogenating agent. Methylene chloride is the preferred solvent although ethylene dichloride may be employed.

It has also been observed to be extremely beneficial that the halogenating agent be as pure as possible. It is believed that some impurities arise in the various halogenating agents due to the multiple oxidation states of the sulfur or phosphorus compound. It has therefore been found desirable to purify the halogenating agent with an unsaturated compounds such as linseed oil, in particular circumstances, squalene. The foregoing materials react with the impurities in the halogenating agents thereby minimizing byproducts and impurities in further reacting the halogenated steroidal acids of the present invention. A tertiary amine such as pyridine has also been useful in obtaining high purity yields of the acid halide.

Following the halogenation of the steroid acid to give the carbonyl halide, the latter material is reacted with a source of ammonia in a sufficient amount to form the corresponding carboxyamido (amide) compounds. The addition of the source of ammonia is conveniently conducted at from about −20° C. to about 80° C., preferably from about −5° C. to about 35° C.

The source of ammonia itself may be any material which conveniently generates ammonia under the reaction conditions specified. Convenient sources of ammonia are either ammonia itself, or ammonium hydroxide. Again, the equivalent amount of ammonia required to convert the carbonyl halide to the carboxyamido compound is employed. Conveniently, however, an excess amount of the source of ammonia may be utilized at convenient levels from about 1:1 equivalents to 5 equivalents, preferably from about 1.2 equivalents to about 3 equivalents.

The reaction of the carbonyl halide with the source of ammonia is conveniently conducted in an organic solvent particularly a halogenated organic solvent such as previously discussed and in particular methylene chloride.

Where ammonium hydroxide is utilized as the source of ammonia, there will, of course, be a substantial amount of water in the reaction mixture which may be otherwise substantially organic in nature. A simple phase separation with a separatory funnel thus allows recovery of substantially all of the desired products from the aqueous phase. The organic phase is then washed several times with water, preferably dried with a material such as calcium sulfate and treated with a convenient filtering agent. The organic solvent employed during the reaction is then removed in any convenient manner. The carboxyamido compound is then further purified by trituration with a material such as acetone to yield the substantially pure carboxyamido compound.

The present invention further contemplates the reaction of the carboxyamido compounds to the corresponding 20-isocyanato compounds.

At this point, the process for preparing the products of the present invention diverges depending on which end products are desired. In one aspect the 20-isocyanate compounds may be obtained and recovered for further processing or the 20-isocyanate compounds may be further reacted in situ to give the corresponding carbamates through the use of an alcohol. Where it is desired to directly recover the 20-isocyanate compounds the following procedure may be utilized.

The carboxyamido compound is reacted in a sufficient equivalent quantity with lead tetraacetate in the presence of a non-aqueous aprotic solvent and thereafter removing the solvent and recovering the 20-isocyanate compound. A solvent is required due to solubility problems and the need to obtain the product on a rapid basis. It is particularly important that an aprotic solvent be utilized during this reaction inasmuch as water or an alcohol would react with the isocyanate as it is formed thus not allowing the isocyanate to be isolated. Conveniently, the reaction is run using tetrahydrofuran as the solvent.

The reaction to form the isocyanate is conveniently conducted at from about 0° C. to about 100° C., preferably from about 5° to about 50° C. The amount of lead tetraacetate employed due to lead effluent regulation should be as little as possible over the amount required on an equivalent basis to form the isocyanate. However, an excess of lead may be used conveniently from about 1.1 equivalents to about 5 equivalents. Preferably, the lead tetraacetate would be utilized at from 1.2 equivalents to about 3 equivalents.

A further desirable variable in conducting the reaction of the carboxyamido compound with lead tetraacetate is that the reaction should be conducted in an inert atmosphere completely free from water. This involves purging the reaction vessel several times with extremely dry nitrogen to remove even trace quantities of water and thereafter blanketing the reaction mixture with dry nitrogen gas.

The solution containing the isocyanate may be washed with sodium thiosulfate and then with a saturated salt solution of sodium chloride to remove any of the lead salts remaining in the reaction mixture. The desired product is then recovered by solvent extraction.

In the second variation of the present invention, the 20-isocyanate compound is not directly recovered but is rather converted through the use of an alcohol to give a carbamic acid ester. The isocyanate may also be converted with a short alkyl chain organic acid such as acetic acid to the corresponding carbamic acid anhydride. That is, where X is replaced in steroids A–D by $NH(CO_2)OCCH_3$ where acetic acid is employed.

The compounds and processes of the present invention are useful in obtaining new steroid intermediates which may be converted to progesterone.

The following are examples of the present invention:

EXAMPLE I

Each of 3-oxo-pregna-1,4-diene-20-carboxylic acid; 3-oxo-pregn-4-ene-20-carboxylic acid; 3-oxo-pregna-1,4,17(20)-triene-20-carboxylic acid; and 3-oxo-pregna-4,17(20)-triene-20-carboxylic acid are obtained and each is run separately through the following reaction. A second run is then conducted using mixtures of the various acids.

The acids are reacted at 0° C. with thionyl chloride using a slight stoichiometric excess of the latter material in methylene chloride. After a period of 20 minutes the reaction is substantially complete and the acid chloride is separated from the byproduct of the reaction. The acid chlorides are isolated and identified.

The foregoing reaction may be conducted using phosphorus trichloride or thionyl bromide to generate the desired acid halides. Small amounts of olefins in the reaction mixture are also seen to improve the process.

EXAMPLE II

Each of the acid halides of Example I are reacted as follows. The following uses the acid chloride for convenience in describing the reaction. The acid amide is generated by reacting the acid chloride with ammonium hydroxide at 0° C. An excess of ammonium hydroxide is employed to increase the reaction rate and to improve the yield. The addition of the ammonium hydroxide to the acid chloride is conducted using methylene chloride as a solvent.

The desired product is recovered using phase separation techniques to isolate the organic phase from the aqueous phase. The aqueous phase may be further extracted with methylene chloride and these extractions then combined with the initial organic phase. The amides generated are then purified by trituration with acetone. The above reaction may be run using ammonia.

The reaction scheme given above generates 3-oxo-pregna-1,4-diene-20-carboxylic acid amide; 3-oxo-pregn-4-ene-20-carboxylic acid amide; 3-oxo-pregna-1,4,17(20)-triene-20-carboxylic acid amide; and 3-oxo-pregna-4,17(20)diene-carboxylic acid amide.

EXAMPLE III

The carboxylic acid amides of Example II are converted to the corresponding 20-isocyanates by reacting the amide with a slight equivalent excess of lead tetraacetate. Tetrahydrofuran is employed as the solvent under a nitrogen atmosphere preceded by a nitrogen purge of the entire system. The mixture of the amide and the lead tetraacetate is stirred for a period of one-half hour at which time the reaction is complete. Sodium thiosulfate is then added to reduce any excess lead salt. The system is washed a second time with the thiosulfate and then three times with saturated sodium chloride.

The solvent is then drawn off leaving the isocyanates. Obtained in this reaction are 20-isocyanato-3-oxo-pregna-1,4-diene; 20-isocyanato-3-oxo-pregn-4-ene; 20-isocyanato-3-oxo-pregna-1,4,17(20)-triene and 20-isocyanato-3-oxo-pregna-4,17(20)-diene.

The carbamic acid esters of each of the foregoing materials are obtained by adding a lower alcohol from methyl through t-butyl to obtain the desired product. The carbamic acid anhydrides are obtained by utilizing a lower acid such as acetic acid.

EXAMPLE IV

An amine is prepared from 20-isocyanato-3-oxo-pregna-1,4-diene. The isocyanate is hydrolyzed using aqueous acetic acid at 65° C. for a period of one hour followed by steam distillation thereby obtaining 20-amino-3-oxo-pregna-1,4-diene acetate salt. The free amine is obtained by using dilute base (sodium hydroxide).

What is claimed is:

1. A process for the production of an amido-steroidal compound selected from the group consisting of 3-oxo-pregna-1,4-diene-20-carboxylic acid amide; 3-oxo-pregn-4-ene-20-carboxylic acid amide; 3-oxo-pregna-1,4,17(20)-triene-20-carboxylic acid amide; and 3-oxo-pregna-4,17(20)-diene-20-carboxylic acid amide and mixtures thereof comprising:
   (a) reacting a member selected from the group consisting of the parent acid of the amido-steroidal compound and mixtures thereof with a sufficient amount of an inorganic halogenating agent to obtain the corresponding carbonyl halide; and,
   (b) reacting the carbonyl halide formed in (a) in the presence of a source of ammonia in a sufficient amount, to form the 3-oxo-pregna-1,4-diene-20-carboxylic acid amide; 3-oxo-pregn-4-ene-20-carboxylic acid amide; 3-oxo-pregna-1,4,17(20)-triene-20-carboxylic acid amide; and 3-oxo-pregna-4,17(20)-diene-20-carboxylic acid amide and mixtures thereof thereby obtaining the desired amido-steroid.

2. The process of claim 1 wherein the parent acid is 3-oxo-pregna-1,4-diene-20-carboxylic acid.

3. The process of claim 1 wherein the parent acid is 3-oxo-pregn-4-ene-20-carboxylic acid.

4. The process of claim 1 wherein the parent acid is 3-oxo-pregna-1,4,17(20)-triene-20-carboxylic acid.

5. The process of claim 1 wherein the parent acid is 3-oxo-pregna-4,17(20)-diene-20-carboxylic acid.

6. The process of claim 1 wherein the halogenating agent is a chlorinating agent.

7. The process of claim 6 wherein the chlorinating agent is thionyl chloride.

8. The process of claim 1 wherein the source of ammonia is ammonium hydroxide.

9. The process of claim 1 wherein the reaction is conducted in the presence of a tertiary amine.

10. The process of claim 1 wherein the reaction is conducted in the presence of methylene chloride.

11. The process of claim 1 wherein the reaction mixture is washed with water and dried over calcium sulfate following the formation of the amiod-steroidal compound.

12. The process of claim 1 wherein the amido-steroidal compounds are purified through trituration with a ketone.

13. The process of claim 1 wherein the source of ammonia is ammonia.

14. 3-oxo-pregna-1,4-diene-20-carboxylic acid amide.

15. 3-oxo-pregna-1,4,17(20)-triene-20-carboxylic acid amide.

16. 3-oxo-pregna-4,17(20)-diene-20-carboxylic acid amide.

17. 3-oxo-pregna-1,4-diene-20-carboxylic acid chloride.

18. 3-oxo-pregna-1,4,17(20)-triene-20-carboxylic acid chloride.

19. 3-oxo-pregna-4,17(20)-diene-20-carboxylic acid chloride.

20. A process for the production of a member selected from the group consisting of 20-isocyanato-3-oxo-pregna-1,4-diene; 20-isocyanato-3-oxo-pregn-4-ene; 20-isocyanato-3-oxo-pregna-1,4,17(20)-triene and 20-isocyanato-3-oxo-pregna-4,17(20)-diene and mixtures thereof from a member selected from the group consisting of 3-oxo-pregna-1,4-diene-20-carboxylic acid amide; 3-oxo-pregna-1,4,17(20)-triene-20-carboxylic acid amide; 3-oxo-pregna-4,17(20)-diene-20-carboxylic acid amide and 3-oxo-pregn-4-ene-20-carboxylic acid amide and mixtures thereof comprising:
   (a) reacting the amide in the presence of a sufficient quantity of lead tetraacetate in the presence of an non-aqueous aprotic solvent;
   (b) thereafter, removing the solvent from the product thereby obtaining the corresponding isocyanate compound.

21. The process of claim 20 wherein the reaction is conducted utilizing tetrahydrofuran as the solvent.

22. The process of claim 20 wherein the conversion of the amide to the isocyanato compound is conducted at from about 0° Celsius to about 100° Celsius.

23. The process of claim 20 conducted under an inert atmosphere.

24. The process of claim 20 wherein the reaction solution is washed with a water soluble thiosulfate solution to reduce any remaining lead tetraacetate in the reaction mixture.

25. 20-isocyanato-3-oxo-pregna-1,4-diene.

26. 20-isocyanato-3-oxo-pregn-4-ene.

27. 20-isocyanato-3-oxo-pregna-1,4,17(20)-triene.

28. 20-isocyanato-3-oxo-pregna-4,17(20)-diene.

29. The process of claim 20 wherein a lower alcohol is subsequently employed to convert the isocyanate to the corresponding carbamic acid ester.

30. 3-oxo-pregna-1,4-diene-20-carbamic acid ester.

31. 3-oxo-pregn-4-ene-20-carbamic acid ester.

32. 3-oxo-pregna-1,4,17(20)-triene-20-carbamic acid ester.

33. 3-oxo-pregna-4,17(20)-diene-20-carbamic acid ester.

34. A process for the production of a carbonyl halide selected from the group consisting of 3-oxo-pregna-1,4-diene-20-carboxylic acid halide; 3-oxo-pregn-4-ene-20-carboxylic acid halide; 3-oxo-pregna-1,4,17(20)-triene-20-carboxylic acid halide; and 3-oxo-pregna-4,17(20)-diene-20-carboxylic acid halide and mixtures thereof comprising reacting the corresponding carboxylic acid with an inorganic halogenating agent to produce the carbonyl halide.

35. The process of claim 34 wherein the carbonyl halide is the carbonyl chloride.

36. The acid anhydrides of a member selected from the group consisting of 3-oxo-pregna-1,4-diene-20-carbamic acid; 3-oxo-pregn-4-ene-20-carbamic acid; 3-oxo-pregna-1,4(20)-triene-20-carbamic acid and 3-oxo-pregna-4,17(20)-diene-20-carbamic acid, and mixtures thereof.

37. 20-amino-3-oxo-pregna-1,4-diene.

* * * * *